United States Patent [19]
Phillipps

[11] 3,933,799
[45] Jan. 20, 1976

[54] 11β-HALO-9,12-UNSUBSTITUTED-$C_{19}$-STEROIDS

[75] Inventor: Gordon Hanley Phillipps, Greenford, England

[73] Assignee: Glaxo Laboratories Limited, Greenford, England

[22] Filed: July 13, 1971

[21] Appl. No.: 162,261

Related U.S. Application Data

[63] Continuation of Ser. No. 795,065, Jan. 29, 1969, abandoned.

[52] U.S. Cl. .................. 260/239.55 R; 260/239.5; 260/239.55 C; 260/397.3; 260/397.4 S; 260/397.5
[51] Int. Cl.² ..................................... C07J 17/00
[58] Field of Search .................. 260/397.45, 397.3

[56]  References Cited
UNITED STATES PATENTS

| | | | |
|---|---|---|---|
| 3,609,171 | 9/1971 | Laurent | 260/397.45 |
| 3,636,011 | 1/1972 | Phillipps et al. | 260/397.3 |
| 3,665,021 | 5/1972 | Elks et al. | 260/397.45 |
| 3,726,864 | 4/1973 | Phillipps et al. | 260/239.55 |
| 3,767,685 | 10/1973 | Van Ulict | 260/397.5 |

*Primary Examiner*—Elbert L. Roberts
*Attorney, Agent, or Firm*—Bacon & Thomas

[57] ABSTRACT

11β-Halo-9α,12-unsubstituted-$C_{19}$-steroids having hormonal activity and a process for preparing same by reacting the corresponding 11α-hydroxy steroid with a compound of the formula

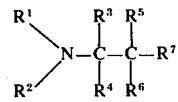

I where $R^1$ and $R^2$ are alkyl groups having 1–8 carbon atoms or aralkyl or aryl groups or, together with the nitrogen atom to which they are attached, comprise a heterocyclic radical;

$R^3$ and $R^4$ are chlorine, bromine or fluorince atoms or a fluorine atom together with a chlorine or bromine atom and $R^5$ is hydrogen or $R^4$ and $R^5$ together represent a carbon-carbon bond;

$R^6$ is a chlorine, bromine or fluorine atom and $R^7$ is a chlorine, bromine or fluorine atom or a trifluoromethyl group, the reaction being effected in the presence of chloride or bromide ions when neither $R^3$ nor $R^4$ is chlorine or bromine.

8 Claims, No Drawings

11β-HALO-9,12-UNSUBSTITUTED-C₁₉-STEROIDS

This is a continuation of application Ser. No. 795,065 filed Jan. 29, 1969, now abandoned.

This invention relates to novel steroids possessing hormonal activity.

In the copending U.S. patent application of Joseph Elks et al Ser. No. 656,665, filed July 28, 1967 and abandoned in favor of a continuation-in-part application Ser. No. 701,064, filed Jan. 29, 1968, which was in turn abandoned in favor of a continuation-in-part application Ser. No. 846,975, filed Aug. 1, 1969, there is described and claimed 9α-unsubstituted-11β-chloro-19-nor-steroids as new compounds having useful hormonal properties, for example progestational or anabolic activity. Copending U.S. patent application of Joseph Elks et al Ser. No. 795,064, filed of even date herewith describes the corresponding 11β-bromo-steroids.

We have now found that such hormonal activity is exhibited by 9α,12-unsubstituted-$C_{19}$-steroids carrying at the 11β-position a halogen atom having an atomic weight between 30 and 85, that is 9α,12-unsubstituted 11β-bromo and 11β-chloro-steroids having a 19-carbon atom, for example steroids possessing the angular methyl group present in the androstanes and pregnanes, in contrast to the 19-nor steroids having no 19-carbon atom. This is a new class of compounds which, surprisingly, can be prepared by the principal chlorination or bromination method described in our said copending applications in spite of steric hindrance from the substituent in the 10-position.

The new steroids according to the invention may carry various ring substituents, for example in the 17-position a hydroxyl group, a protected hydroxyl group, an oxo group, or a protected oxo group, or an aliphatic, araliphatic, acyl or acyloxyacyl group in the presence or absence of a hydroxyl or protected hydroxyl group; in the 16-position a methyl, methylene or methoxy group; in the 6-position a chlorine or fluorine atom or a methyl group; in the 3-position an oxo, protected oxo, hydroxyl or protected hydroxyl group. The carbon atoms in the 16- and 17- positions may carry an epoxide or methylene group or form part of a 1'-pyrazolino-(4',3':16α,17α) or 2'-pyrazolino-(4',5':16α,17α)-grouping. The steroids may possess double bonds; for example, the A-ring may possess double bonds in the 1,2-position and/or the 4,5-position. The B-ring may also be unsaturated, for example with a double bond in the 5,6- or 6,7-position. The D-ring may also possess a double bond in the 16,17-position.

The terms 'protected hydroxyl' or 'protected oxo' groups include such groups as acyloxy, alkoxy, ketal or enol ether groups which groups may be converted subsequently to oxo or hydroxyl groups or, alternatively, may be allowed to remain unchanged in the final product.

Where acyloxy groups are present as protected hydroxyl groups, these may be substituted or unsubstituted aliphatic, cycloaliphatic, araliphatic or aryl acyloxy groups, for example acetoxy, valeryloxy, propionyloxy, hexahydrobenzoyloxy, β-phenylpropionyloxy, benzoyloxy or isobutyryloxy groups.

Other protected hydroxyl groups include ethers, e.g. alkoxy groups having 1–5 carbon atoms, or aralkoxy or aryloxy groups, especially arylmethoxy groups such as benzyloxy groups. Protected oxo groups include ketal groups, e.g. ethylene dioxy groups and enol ether groups such as enol methyl ether groups.

The aliphatic groups which may be present in the 17-position preferably contain 1–9 carbon atoms and may, for example, be substituted and/or contain unsaturation. Substituents which may be present include for example, halogen atoms (e.g. chlorine) or hydroxy or acyloxy groups. Useful aliphatic substituents thus include methyl, ethyl, propyl, vinyl, 2-methyl-prop-2-enyl, 1-methyl-prop-2-enyl, but-2-enyl, allyl, ethynyl or chloroethynyl groups.

All the steroids according to the present invention possessing a 4,5-double bond show progestational activity.

Particularly useful steroids according to the invention include steroids having a 3-oxo-group and a 4,5-double bond or double bonds in both 4,5- and 6,7-positions or a 3-acyloxy or 3-ether group and double bonds in the 3,4- and 5,6-positions. This type of compound in general possesses progestational and antioestrogenic activity with or without antiandrogenic activity. A 6-methyl or 6-chloro substituent often enhances such activity.

Compounds of this type include, for example, 11β-chloropregn-4-ene,-3,20-dione, 17α-acetoxy-11β-chloro-pregn-4-ene-3,20-dione and 17α-acetoxy-11β-chloro-6-methylpregn-4,6-diene-3,20-dione.

Another particularly useful group of compounds according to the invention are those possessing a 3-oxo group and double bonds in the 1,2- and 4,5-positions, and especially such 1,4-dienes possessing a 17- and/or 21-ester grouping or a 17,21-ortho ester or ketonide grouping. The compounds of this type possess in addition to some progestational activity valuable topical anti-inflammatory activity which is in general greater than that of the corresponding 11-unsubstituted compounds. The ratio of topical to undesired systemic activity is good and has been found to exceed that of 6α-fluorotriamcinolone acetonide for the compounds which have been tested. A 16-methyl or 16-methylene group is found to enhance such activity.

The ester groupings which may advantageously be present at the 21- and/or 17- positions include acyloxy groupings, for example, aliphatic acyloxy groups such as acetoxy, propionyl-oxy, butyryloxy, isobutyryloxy or valeryloxy groups which may carry substituents such as carboxyl groups, and araliphatic and aromatic acyloxy groupings. Other ester groups include phosphate ester groups which generally impart a degree of water solubility to the product.

The 17,21-ortho ester groupings may, for example, be lower alkyl ortho-lower aliphatic acyl groups. 17,21-Ketonides include, for example, acetonides, methylethyl-ketonides etc. Particularly interesting antiinflammatory compounds include 11β-chloro-21-hydroxy-17α-propionyloxy-16β-methylpregna-1,4-diene-3,20-dione, 11β-chloro-21-acetoxy-17-propionyloxy-16β-methyl-pregna-1,4-diene-3,20-dione and 11β-chloro-17,21-dipropionyloxy-16β-methylpregna-1,4-diene-3,20-dione.

The new compounds according to the invention may be prepared in any convenient way. According to a further feature of the invention we provide a process for the preparation of 9α,12-unsubstituted-$C_{19}$-steroids carrying at the 11β position a halogen atom having an atomic weight between 30 and 85, in which a corresponding 9α,12-unsubstituted-11α-hydroxy-$C_{19}$-steroid is reacted with a compound of the general formula

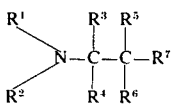

where $R^1$ and $R^2$, which may be the same or different, are alkyl groups having 1–8 carbon atoms or aralkyl or aryl groups or, together with the nitrogen atom to which they are attached, comprise a heterocyclic radical which may, if desired, contain further hetero-atoms, $R^3$ and $R^4$ both being chlorine, bromine or fluorine atoms or a fluorine atom together with a chlorine or bromine atom and $R^5$ is hydrogen or $R^4$ and $R^5$ together represent a carbon-carbon bond;

$R^6$ is a chlorine, bromine or fluorine atom and $R^7$ is a chlorine, bromine of fluorine atom or a trifluoromethyl group, the reaction being effected in the presence of chloride or bromide ions when neither $R^3$ nor $R^4$ is chlorine or bromine.

Where $R^3$ and/or $R^4$ are chlorine or bromine, the compound of formula I acts directly as a chlorinating agent or brominating agent but where neither $R^3$ nor $R^4$ is chlorine or bromine, it is necessary to carry out the reaction in the presence of chloride or bromide ions. While it is not wished to be bound by theoretical considerations it is believed that the reagent of formula I reacts with the 11α-hydroxy group to form an intermediate ether with liberation of $HR^3$ or $HR^4$, whereupon the resultant nucleophilic ions $R^{3-}$ or $R^{4-}$ attack the ether grouping to split off the residue of the reagent I and introduce halogen at the 11-position. The chloride and bromide ions are more strongly nucleophilic than the fluoride ion so that even when neither $R^3$ nor $R^4$ is chlorine or bromine, reaction in the presence of chloride or bromide ions results in the introduction of chlorine or bromine at the 11-position.

The reaction according to the invention is particularly useful because no methods have previously been described for the preparation of 12-unsubstituted 11β-chloro or bromo-$C_{19}$-steroids with a 9α-hydroxy atom and the method previously proposed for production of the analogous 11β-fluoro-steroids in the $C_{19}$ series having a 9α-hydrogen atom tends to give the 9,11-unsaturated product.

The source of chloride or bromide ions in the variation of the reaction in which neither $R^3$ nor $R^4$ is chlorine or bromine is preferably a salt soluble in organic solvents but the cationic portion should be inert to the reagent of formula I for example, the cation of a tertiary or quaternary nitrogen base, e.g. triethylamine, trimethylamine, pyridine, collidine, or tetrabutylammonium hydroxide. In general, however, the preferred source of chloride or bromide ions is lithium chloride or bromide.

The reagents of formula I in which neither $R^3$ nor $R^4$ is chlorine or bromine include N-(2-chloro-1,1,2-trifluoroethyl) diethylamine, N-(1,1,2,2-tetrafluoroethyl)diethylamine, N-(2-chloro-1,1,2-trifluoroethyl)-dimethylamine, N-(2-chloro-1,1,2-trifluoroethyl)dipropylamine, N-(2-chloro-1,1,2-trifluoroethyl)-diisobutylamine, N-(2-chloro-1,1,2-trifluoroethyl)dioctylamine, N-(2-chloro-1,1,2-trifluoro-ethyl)methylethylamine, N-(2,2-dichloro-1,1-difluoroethyl) diethylamine, N-(1,1,2,3,3,3-hexafluoropropyl)diethylamine and N-(1,1,2,2-tetrafluoroethyl)diisopropylamine. The reagent of choice is N-(2-chloro-1,1,2-trifluoroethyl)-diethylamine.

Reagents of formula I in which one or both of $R^3$ and $R^4$ are chlorine include, in particular, N,N-diethyl-trichloro-vinylamine.

The reaction is preferably effected in an inert solvent that is any solvent which does not react with the reagent of formula I. Such solvents comprise, for example, aromatic and aliphatic hydrocarbons, halogenated hydrocarbons, esters, ketones, nitriles, ethers and tertiary alcohols. Examples of such solvents are benzene, toluene, chlorobenzene, methylene chloride, pentane, hexane, cyclohexane, ethyl acetate, butyl acetate, acetonitrile, acetone, methyl ethyl ketone, tetrahydrofuran, diethyl ether, diethylene glycol dimethyl ether, t-butyl alcohol, t-amyl alcohol and the like. Since the starting materials are frequently only slightly soluble in nonpolar solvents, a polar solvent such as tetrahydrofuran is preferred.

Unless further chlorine or bromine substituents are required, reactive hydroxyl groups initially present in the steroid should be protected, for example by esterification, etherification etc.

Particularly preferred starting compounds are the 11α-hydroxy-3-oxo-$\Delta^4$-$C_{19}$-steroids.

The 9α-unsubstituted-11α-hydroxy-$C_{19}$-steroids may be prepared in any convenient way. Thus, for example, the 11α-hydroxy group may be introduced into a $C_{19}$-steroid having no 11-substituent by microbiological methods e.g. using organisms such as *Aspergillus ochraceus* and *Rhizopus nigricans*.

The foregoing reaction to introduce the 11β-chlorine or bromine atom may be carried out on an 11α-hydroxy steroid which possesses the various substituents intended in the final product or such substituents may be introduced in subsequent reaction stages. Applications Ser. No. 656,665 and 795,064, mentioned earlier, describe the introduction of an 11β-chlorine or bromine atom into 3-oxo-$\Delta^4$-19-nor steroids and a series of subsequent reactions which allow other groupings in the A, B and D rings to be introduced, for example 3-enol ether groupings, 3-oxo-$\Delta^{4,6}$-groupings, 17α-acyloxy groupings or 17α-hydrocarbon-17β-hydroxy groupings, e.g. 17α-ethynyl or alkyl groupings. Methods are also described for the introduction of 16-methyl, 16-methylene, 16-methoxy, $\Delta^{16}$, 16,17-epoxy, and 16,17-methylene,1'-pyrazolino(4',3':16α,17α)- and 2'-pyrazolino-(4',5':16α,17α) groupings.

For the preparation of 17-esters and also 17,21-diesters, ortho esters and ketonides in the pregnane series, one can react an 11α-hydroxy-steroid having the required ester groupings with the reagent of formula I. Alternatively, one can take advantage of the fact that the tertiary alcohol grouping in 17α-hydroxy steroids does not enter into this reaction so that an 11α-17α-dihydroxy pregnane will react to give an 11β-chloro17α-hydroxy pregnane which can subsequently be reacted with an esterifying agent. Where a 17,21-diester is required, however, the 21-ester grouping is preferably present initially. The 17-hydroxy group can be subsequently esterified, for example, by reaction with such esterifying reagents as acyl halides or anhydrides, e.g. acetic, propionic or benzoic anhydride or chloride. If a 3-oxo or 3-oxo-$\Delta^4$-grouping is present, the corresponding enol or dienol ester may be formed that is a 3-acyloxy-$\Delta^2$ or $\Delta^3$-grouping or a 3-acyloxy-$\Delta^{3,5}$-grouping. The resulting steroid can readily be hydrolysed, however, to regenerate the 3-oxo-grouping without removing the 17-acyloxy group, e.g. using methanolic alkali. One useful reagent for acetylation is isopropenyl acetate with an acid catalyst.

It is also possible to acylate a 17α-hydroxy steroid without affecting a 3-oxo-$\Delta^4$-grouping by using as acylating agent trifluoroacetic anhydride and the appropriate acid, for example a lower aliphatic acid such as acetic or propionic acid.

A particularly useful route to 17-acyloxy-21-hydroxy steroids is to react a 17,21-diol with a tri-lower alkyl ortho ester of the appropriate carboxylic acid, preferably in the presence of an acid catalyst, to form the corresponding orthoester. This ortho-ester may then be hydrolysed, for example under acid conditions e.g. using a dilute mineral acid, to yield the desired 17-acyloxy-21-hydroxy steroid. The 17,21-ortho esters are themselves, of course, useful anti-inflammatory compounds. This route avoids difficulties in esterifying the 17-hydroxy group in the presence of the 3-oxo-$\Delta^4$-system and 17,21-diesters can be produced from a 17-hydroxy-21-ester produced initially by the halogenation process by first hydrolysing the 21-acyloxy group forming a 17,21-orto-ester, hydrolysing the latter and esterifying the 21-hydroxy group.

17,21-Ketonides can be prepared by reaction of the corresponding 17,21-diol with the appropriate ketone in the presence of an acid catalyst, for example a Lewis acid such as boron trifluoride.

According to a still further feature of the invention we provide pharmaceutical compositions comprising one or more of the steroids according to the invention together with a pharmaceutical carrier or excipient and/or one or more further active compounds. Compounds having progestational activity can advantageously be formulated with one or more oestrogens.

The compositions according to the invention are intended for administration to both humans and animals. The term "pharmaceutical" as used herein to describe compositions and carriers means therefore that these are of use in both human and veterinary medicine.

Steroids possessing topical anti-inflammatory activity may be formulated into preparations suitable for topical application in conventional manner with the aid of one or more carriers or excipients. Examples of various types of preparation include ointments, lotions, creams, powders, aerosols, sprays, drops, suppositories and retention enemas, and chewable and suckable tablets or pellets (e.g. for the treatment of aphthous ulcers). Ointments and creams may, for example be formulated with an aqueous or oily base with the addition of suitable thickening and/or gelling agents. Such bases may thus, for example, include water and/or an oil such as liquid paraffin or a vegetable oil such as arachis oil or castor oil. Thickening agents which may be used according to the nature of the base include soft paraffin, alluminium stearate, cetostearyl alcohol, polyethylene glycols, wool-fat, hydrogenated lanolin, beeswax etc.

Lotions may be formulated with an aqueous or oily base and will in general also include one or more of the following namely, emulsifying agents, dispersing agents, suspending agents, thickening agents, colouring agents, perfumes and the like.

Powders may be formed with the aid of any suitable powder base e.g. talc, lactose, starch etc. Drops may be formulated with an aqueous base also comprising one or more dispersing agents, suspending agents, solubilising agents etc.

Spray compositions may for example be formulated as aerosols with the use of a suitable propellant, e.g. dichlorodifluoromethane or trichlorofluoromethane.

The proportion of active steroid in the topical compositions according to the invention depends on the precise type of formulation to be prepared but will generally be within the range of from 0.0001% to 5% by weight. Generally however for most types of preparations advantageously the proportion used will be within the range of from 0.001 – 0.5% and preferably 0.01 to 0.25%.

For internal anti-inflammatory action, the anti-inflammatory compounds may be administered in oral, rectal vaginal or parenteral formulations.

Steroids possessing progestational or other hormonal activity may be formulated into compositions for oral, vaginal, rectal or parenteral administration. Such compositions are preferably in the form of dosage units. They may be formulated for daily oral administration in such forms as tablets, capsules, sachets etc., either for taking directly or with a draught. Suppositories for rectal or vaginal absorption may also be employed. Injection preparations may be formulated, preferably for more prolonged action, while implantation pellets may be formulated having the advantage of requiring very infrequent administration.

Conventional pharmaceutical excipients for solid preparations may for instance include sugar alcohols, sugars, starch, magnesium stearate, gelatine, polyethylene glycols and suitable colouring agents. Tablets may be coated for protection, colour distinction or elegance by conventional methods such as film coating or sugar or pearl coating. Suppositories may be prepared, using conventional bases such as glyco-gelatine, cocoabutter, or water-dispersible bases with a melting point above body temperature, such as polyglycols.

For injection purposes, preparations for intramuscular or subcutaneous administration may be prepared in conventional sterile oily, aqueous or emulsion bases, in solution and/or suspension. Vehicles preferably include physiologically acceptable vegetable oils, e.g. arachis oil, fractionated coconut oil; oily esters, e.g. isopropyl myristate; nonaqueous solvents, e.g. propylene glycol; aqueous vehicles such as sterile water or physiological saline; together with suitable formulatory agents such as suspending agents, e.g. aluminium stearate for oily materials, carboxymethyl cellulose for aqueous preparations; physiologically acceptable emulsifying agents, e.g. "Tween" 81, buffering agents for pH control, antioxidants, stabilising and solubilising agents. The injections may be formulated for immediate use, or as a dry powder for re-constitution before use with a separate vehicle. Unit injections required for prolonged action, e.g. 1 month's duration, would naturally contain an increased quantity of active material.

Each dosage unit for daily administration to humans preferably contains 0.05 to 5.0 mg. active material according to the invention, advantageously 0.2 to 2.0 mg.

Implantation pellets would in general contain a much higher dosage to cover prolonged activity for preferably several months. Implants may be prepared aseptically from sterile material, by fusion or heavy compression, preferably without the addition of other substances.

For veterinary use in particular, long acting vaginal inserts such as tampons and pessaries may be prepared in a conventional manner. The dosage required for animal treatment will of course, vary according to the size of the animal.

The compositions according to the invention may also include one or more preservatives or bacteriostatic agents e.g. methyl hydroxy benzoate, propyl hydroxy benzoate, chlorocresol or benzalkonium chlorides. The compositions according to the invention may also contain other active ingredients such as antimicrobial agents, particularly antibiotics, such as neomycin.

The following Examples are given by way of illustration only, all temperatures are in degrees centrigrade:-

EXAMPLE 1

11β-Chloropregn-4-ene-3,20-dione

A mixture of 11α-hydroxy progesterone (6 g., 0.018 mole), anhydrous lithium chloride (6 g., 0.14 mole), N-(2-Chloro-1,1,2-trifluoroethyl)diethylamine (6 ml., 0.036 mole) and dry tetrahydrofuran (120 ml.) was stirred at −20° for 5 hr. and then room temperature for 16 hr. The reaction mixture was partitioned between methylene chloride and water. Evaporation of the organic layer and chromatography of the residue on magnesium silicate afforded, after recrystallisation from acetone/petroleum ether (b.p. 60°–80°), 11β-chloropregn-4-ene-3,20-dione (0.26 g., 4%), m.p. 185°–188° $[\alpha]_D + 252°$ (c 1.0 $CHCl_3$), $\lambda_{max}$. (EtOH) 238 nm. ($\epsilon$ 17,150).

EXAMPLE 2

11β-Chloro-17α-hydroxypregn-4-ene-3,20-dione

A mixture of 11α,17α-dihydroxyprogesterone (9.26 g., 0.027 mole), anhydrous lithium chloride (9.25 g., 0.22 mole), N-(2-chloro-1,1,2-trifluoroethyl)diethylamine (9.26 ml., 0.056 mole) and dry tetrahydrofuran (270 ml.) was stirred at 0° for 2 hr. The reaction mixture was poured into ice/water (2 l.) and the precipitate was then filtered off. Chromatography of the product on magnesium silicate, afforded, after recrystallisation from acetone. 11β-chloro-17α-hydroxypregn4-ene-3,20-dione (6%), m.p. 193°-196°, $[\alpha]_D + 149°$ (c. 0.75, $CHCl_3$), $\lambda_{max}$. (EtOH) 238 nm. ($\epsilon$ 16,400).

EXAMPLE 3

17α-Acetoxy-11β-chloropregn-4-ene-3,20-dione

11β-Chloro-17α-hydroxypregn-4-ene-3,20-dione (0.365 g. 0.001 mole) in refluxing dry benzene (20 ml.) was treated under a stream of dry nitrogen with isopropenyl acetate (3 ml, 0.027 mole) and toluene-p-sulphonic acid (0.02 g.). The solution was slowly distilled for 5 hrs; benzene/isopropenyl acetate (10:1) being added to maintain constant volume. Pyridine (0.3 ml.) was added and the reaction mixture was then partitioned between benzene and water. Evaporation of the organic layer afforded 11β-chloro-3,17α-diacetoxy-pregna-3,5-dien-20-one (0.449 g.) which was then dissolved in tetrahydrofuran (40 ml.) and treated with methanolic potassium hydroxide (11.8 ml of 0.085 N; 1 mole equiv.). After 5 mins. at room temperature the solution was partitioned between ether and water. Evaporation of the organic layer and preparative thin-layer chromatography of the residue afforded, after recrystallisation from acetone/petroleum ether (b.p. 60°–80°), 17α-acetoxy-11β-chloropregn-4-ene-3,20-dione (0.14 g., 35%), m.p. 170°–173° (decomp.) $[\alpha]_D$ + 104° (c 0.5, $CHCl_3$), $\lambda_{max}$. (EtOH) 238 nm. ($\epsilon$ 13,600).

EXAMPLE 4

21-Acetoxy-11β-chloro-17α-hydroxy-16β-methyl-pregn-1,4-diene-3,20-dione

21-Acetoxy-11α,17α-dihydroxy-16β-methylpregna-1,4-diene-3,20-dione (2.5 g., 6 mmole), lithium chloride (2.5 g.) and N-(2-chloro-1,1,2-trifluoroethyl) diethylamine (2.5 ml.) in dry tetrahydrofuran (55 ml.) was stirred at 0° for 2½ hr. The reaction mixture was then poured into water (500 ml.) and the solid (2.62 g.) was collected by filtration.

A portion of the crude product (1.34 g.) was purified by preparative layer chromatography and crystallisation from acetone/petroleum ether (b.p. 60°–80°) to give 21-acetoxy-11β-chloro-17α-hydroxy-16β-methyl-pregna-1,4-diene-3,20-dione. (0.27 g., 20%), m.p. 194° (decomp.), $[\alpha]_D$ + 168° (c 0.8 $CHCl_3$), $\lambda_{max}$. (EtOH) 241 nm ($\epsilon$ 15300).

EXAMPLE 5

11β-Chloro-17,21-dihydroxy-16β-methylpregna-1,4-diene-3,20-dione

A solution of 21-acetoxy-11β-chloro-17-hydroxy-16β-methylpregna-1,4-diene-3,20-dione (100 mg.) in methanol (7 ml.) was treated with 60% aqueous perchloric acid (0.2 ml.) at room temperature. After 24 hours sodium acetate (100 mg.) was added and about half of the solvent was evaporated in vacuo. Purification of the remaining solution by preparative thin layer chromatography and crystallisation from methanol afforded 11β-chloro-17,21-dihyroxy-16β-methylpregna-1,4-diene-3,20-dione as needles, m.p. 202°–204° decomp (Kofler).

EXAMPLE 6

11β-Chloro-17,21-(1′-ethoxy-1′-ethylmethylenedioxy)-16β-methyl-pregna-1,4-diene-3,20-dione.

A solution of 11β-chloro-17,21-dihydroxy-16β-methyl-pregna1,4-diene-3,20-dione (47 mg.) in dioxan (2 ml.) was treated with ethyl orthopropionate (0.05 ml.) and toluene p-sulphonic acid (5 mg.) at room temperature. After 30 minutes a little sodium bicarbonate was added and the mixture was then diluted with dilute sodium bicarbonate solution. The precipitated oily material was extracted with ethyl acetate, washed with water and the solvent removed in vacuo to afford 11β-chloro-17,21-(1′-ethoxy-1′-ethylmethylenedioxy)-16β-methylpregna-1,4-diene-3,20-dione which showed $R_F$ 0.8 on thin layer chromatography on silica in chloroform - acetone (3:1).

EXAMPLE 7

11β-Chloro-21-hydroxy117-propionyloxy-16β-methyl-pregna-1,4-diene-3,20-dionee.

The above 17,21-ethyl orthopropionate in acetone (2 ml.) was treated with 0.08 N sulphuric acid (0.4 ml.) and the mixture was kept at room temperature for 20 minutes. The clear solution was diluted with water and extracted with ethyl acetate to give the crude 17-ester as an oil. Crystallisation from ether afforded 11β-chloro-21-hydroxy-16β-methyl-17-propionyloxypregna-1,4-diene-3,20-dione as needles, m.p. 164°–165°

(Kofler), $\nu_{max}$. (in bromoform) 3440, 1720, 1655 and 886 cm.$^{-1}$.

EXAMPLE 8

21-Acetoxy-11β-chloro-16β-methyl-17-propionyloxypregna-1,4-diene-3,20-dione

A solution of 11β-chloro-21-hydroxy-16β-methyl-17-propionyloxypregna-1,4-diene-3,20-dione (75 mg) in pyridine (1 ml) was treated with acetic anhydride (0.2 ml) at room temperature. After 3 hours water (0.4 ml) was added and the solution was poured into dilute by hydrochloric acid. The precipitated solid was removed by filtration and after drying was recrystallized from methanol to give the title compound, m.p. 212°–213°(K), $[\alpha]_D$ + 101.1° (c 0.6 chloroform). $\lambda_{max}$ 239 nm (ε 16,280) (Found: C, 65.7; H, 7.0; Cl, 6.8. $C_{27}H_{35}ClO_6$ requires C, 66.0; H, 7.2, Cl, 7.2%).

EXAMPLE 9

11β-Chloro-16β-methyl-17,21-dipropionyloxypregna-1,4-diene-3,20-dione

A solution of 11β-chloro-21-hydroxy-16β-methyl-17-propionyloxypregna-1,4-diene-3,20-dione(75 mg) in pyridine (1 ml) was cooled to 0° and treated with stirring with propionyl chloride (0.04 ml). After 90 minutes a little water was added and the solution poured into dilute hydrochloric acid. The precipitated solid was removed by filtration and recrystallized from methanol to give the title compound, m.p. 220°–222° (K), $[\alpha]_D$ + 105° (c 0.6, chloroform) $\lambda_{max}$ 240nm (ε 15,060) (Found C, 65.9; H, 7.2; Cl, 6.7. $C_{28}H_{37}ClO_6$ requires C, 65.7; H, 7.55; Cl, 7.0%).

EXAMPLE 10

21-Butyryloxy-11β-chloro-16β-methyl-17-propionyloxypregna-1,4-diene-3,20-dione

A solution of 11β-chloro-21-hydroxy-16β-methyl-17-propionyloxypregna-1,4-diene-3,20-dione (75 mg.) in pyridine (1 ml) at room temperature was treated with butyric anhydride (0.3 ml.). After four hours a little water was added and the solution poured into dilute hydrochloric acid. Filtration of the precipitated solid and crystallization from methanol afforded the title compound, m.p. 228°–229° (K), $[\alpha]_D$ + 104.4° (c 0.6 chloroform) $\lambda_{max}$ 239 nm (ε 16,160) (Found: C, 67.1; H, 7.6; Cl, 6.4. $C_{29}H_{39}ClO_6$ requires C, 67.1; H, 7.55; Cl, 6.85%).

EXAMPLE 11

11β-Chloro-21-hydroxy-17-isobutyryloxy-16β-methyl-pregna-1,4-diene3,20-dione

A solution of 11β-chloro-17,21-dihydroxy-16β-methylpregna-1,4-diene-3,20-dione (214 mg.) in dioxan (7 ml.) was treated with trimethyl orthoisobutyrate (0.22 ml.) and toluene p-sulphonic acid (23 mg.) at room temperature. After 45 minutes a little sodium bicarbonate was added and the mixture was then poured into a dilute solution of sodium bicarbonate. The oily product was extracted into ethyl acetate and washed with water. Evaporation of the organic solent gave an oil which was dissolved in acetone (10 ml.) and treated with 0.08 N-sulphuric acid (2.4 ml.). After keeping at room temperature for 30 minutes, the solution was diluted with water and the precipitated oil was extracted with ethyl acetate and washed with water. Evaporation of the organic solvent afforded the crude product which, on crystallization from ether-petroleum ether, gave the title compound, m.p. 163°–164° (K), $[\alpha]_D$ + 108.5 (c 0.6 chloroform) $\lambda_{max}$ 240 nm (ε 15,460) (Found: C, 67.7; H, 7.7; Cl, 7.4. $C_{26}H_{35}ClO_5$ requires C, 67.45; H, 7.6; Cl, 7.65%).

EXAMPLE 12

21-Acetoxy-11β-chloro-17-isobutyryloxy-16β-methyl-pregna-1,4-diene-3,20-dione

Acetic anhydride (0.22 ml.) was added to a solution of 11β-chloro-21-hydroxy-17-isobutyryloxy-16β-methylpregna-1,4-diene-3,20 dione (71 mg.) in pyridine (1 ml.) at room temperature. After 3.5 hours, a little water was added and the solution was poured into dilute hydrochloric acid. Filtration of the precipitated solid and crystallization from methanol afforded the title compound, m.p. 204°–205° (K), $[\alpha]_D$ + 95.2 (c 0.6 chloroform) $\lambda_{max}$ 240 nm (ε 15,450) (Found: C, 67.05; H, 7.4; Cl, 7.05, $C_{28}H_{37}ClO_6$ requires C, 66.6; H, 7.4; Cl, 7.0%).

EXAMPLE 13

11β-Chloro-17β-isobutyryloxy-16β-methyl-21-propionyloxy-pregna-1,4-diene-3,20-dione Propionyl chloride (0.03 ml.) was added to a stirred solution of 11β-chloro-21-hydroxy-17-isobutyryloxy-16β-methylpregna-1,4-diene-3,20-dione (70 mg.) in pyridine (1 ml.) at 0°. A little water was added after one hour and the solution diluted with dilute hydrochloric acid. The precipitate was collected by filtration and recrystallized from methanol to yield the title compound, m.p. 192°–194° (K) $[\alpha]_D$ + 101.5° (c 0.62 chloroform) $\lambda_{max}$ 240 nm (ε 15,460) (Found: C, 66.8; H, 7.5; Cl, 6.8. $C_{29}H_{39}ClO_6$ requires C, 67.1; H, 7.6; Cl, 6.8%).

EXAMPLE 14

17-Acetoxy-11β-chloro-21-hydroxy-16β-methylpregna-1,4-diene-3,20-dione

Prepared by the method described in Example 11, but using triethyl orthoacetate in place of trimethyl orthoisobutyrate. The crude product was crystallized from acetone-petroleum ether to afford the title compound, m.p. 188°–190° (K), $[\alpha]_D$ + 121.2° (c 0.6 chloroform) $\lambda_{max}$ 240 nm (ε 15,280) (Found: C, 65.7; H, 7.1; Cl, 8.1. $C_{24}H_{31}ClO_5$ requires C, 66.3; H, 7.2; Cl, 8.15%).

EXAMPLE 15

17-Acetoxy-11β-chloro-16β-methyl-21-propionyloxy-pregna-1,4-diene-3,20-dione

A solution of 17-acetoxy-11β-chloro-21-hydroxy-16β-methylpregna-1,4-diene-3,20-dione (67 mg.) in pyridine (1 ml.) at 0° was treated with propionyl chloride (0.03 ml.). After one hour, a little water was added and the solution was diluted with dilute hydrochloric acid. The precipitated solid was collected and recrystallized from methanol to give the title compound, m.p. 213°–215° (K), $[\alpha]_D$ + 108.4° (c 0.6, chloroform) $\lambda_{max}$ 240 nm (ε 15,760) (Found: C, 65.9; H, 7.2. $C_{27}H_{35}ClO_6$ requires C, 66.0; H, 7.2).

EXAMPLE 16

17-Acetoxy-11β-chloro-21-isobutyryloxy-16β-methylpregna-1,4-diene-3,20-dione

A solution of 17-acetoxy-11β-chloro-21-hydroxy-16β-methylpregna-1,4-diene-3,20-dione (70 mg.) in pyridine (1 ml) was treated with isobutyric anhydride (0.3 ml.) at room temperature. After 3 hours, a little water was added and the solution was then diluted with dilute hydrochloric acid. The solid was collected and recrystallized from methanol to give the title compound, m.p. 193°–194° (K), $[\alpha]_D$ + 104.3° (c 0.6 chloroform) $\lambda_{max}$ 240 nm ($\epsilon$ 16,020) (Found: C, 66.55; H, 7.3; Cl, 7.0. $C_{28}H_{37}Cl\ O_6$ requires C, 66.6; H, 7.4; Cl, 7.0%).

EXAMPLE 17

11α,17α-Dihydroxy-6-methylpregna-4,6-diene-3,20-dione

17α-Hydroxy-6-methylpregna-4,6-diene-3,20-dione (80 mg.) dissolved in dimethyl sulphoxide (8 ml.) was added to a 24 hr. growth of *Aspergillus Ochraceus* NRRL 405 suspended in water (320 ml.) in a 2L Shake flask. After 72 hrs. at 28° on a rotary shaker the mycelium was filtered off and the filtrate was extracted with ethyl acetate and evaporated to give a gum (100 mg.). This was subjected to preparative layer chromatography using silica gel and chloroform/ethanol 9:1; crystallization from methyl acetate gave 11α,17α-dihydroxy-6-methylpregna-4,6-diene-3,20-dione (25 mg.) m.p. 210°–213°, $\lambda_{max}$ (in EtOH) 290 nm.

EXAMPLE 18

11β-Chloro-17α-hydroxy-6-methylpregna-4,6-diene-3,20-dione

11α,17α-Dihydroxy-6-methylpregna-4,6-diene-3,20-dione (0.35 g.) in stirred, dry tetrahydrofuran (6 ml.) was treated at room temperature with anhydrous lithium chloride (0.35 g.) and N-(2-chloro-1,1,2-trifluoroethyl)diethylamine (0.35 ml.). After 1 hr. the reaction mixture was partitioned between water and methylene chloride. The organic layer was evaporated and the residue was purified by preparative layer chromatography to yield the title compound as a foam (0.156g., 43%). Trituration with methyl acetate gave crystals, m.p. 179°–182° (dec.) $\lambda_{max}$ (in EtOH) 286.5 nm ($\epsilon$ 22,300).

EXAMPLE 19

17α-Acetoxy-11β-chloro-6-methylpregna-4,6-diene-3,20-dione

11β-Chloro-17α-hydroxy-6-methylpregna-4,6-diene-3,20-dione (0.148 g.) in glacial acetic acid (2 ml.) was treated with trifluoroacetic anhydride (0.4 ml.). After 2 hrs. at 80°, the reaction mixture was partitioned between water and methylene chloride. The organic layer was evaporated and the residue was partially purified by preparative layer chromatography to give the crude acetate (0.113 g., 69%) $\lambda_{max}$ (in EtOH) 286 nm ($E_{1cm}^{1\%}$ 580).

The following Examples illustrate pharmaceutical compositions according to the invention (all % values are by weight):

A. Oral Tablets (for intermittent administration)

| | |
|---|---|
| (a) 17α-acetoxy-11β-chloro-6-methylpregna-4,6-diene-3,20-dione | 2.0 mg |
| (b) Ethynyl oestradiol | 0.1 mg |
| Starch (60 mesh B.S.) | 10.5 mg |
| Lactose (60 mesh B.S.) | 66.6 mg |
| Magnesium stearate (100 mesh B.S.) | 0.8 mg |
| | 80.0 mg |

Ball mill (a) and (b) separately with very small quantities of lactose, mix together and dilute with 5 successive portions of lactose, milling between each. Triturate with the starch and blend in the remaining lactose to form a homogeneous powder. Granulate with 50% ethanol in water and pass through a No. 12 mesh B.S. sieve. Dry the granules to constant weight and pass through a No. 20 mesh B.S. sieve and blend in the magnesium stearate prior to compression at 80 mg. per tablet on 7/32 inch punches, preferably engraved punches for identification of the tablets. Pressure is adjusted so that the tablets disintegrate within 10 mins. The tablets may be film coated for colour distinction.

B. Ointment

| | |
|---|---|
| 11β-Chloro-17,21-dihydroxy-16β-methylpregna-1,4-diene-3,20-dione 17-propionate 21-acetate | 0.125% |
| Liquid paraffin B.P. | 10.0% |
| White soft paraffin to | 100% |

Ball mill the steroid with a little of the liquid paraffin until the particle size is reduced to a maximum of 5μ and preferably mainly below 2μ. Dilute the paste and rinse out the mill with the remaining liquid paraffin, mix and add the suspension to the melted white soft paraffin at 50°C. Stir until cold to give a homogeneous ointment.

C. Cream (water-miscible)

| | |
|---|---|
| 11β-Chloro-17,21-dihydroxy-16β-methylpregna-1,4-diene-3,20-dione 17-propionate 21-acetate | 0.1% |
| Beeswax | 15.0% |
| Cetostearyl alcohol | 7.0% |
| Cetomacrogol 1000 B.P.O. | 3.0% |
| Liquid paraffin | 5.0% |
| Chlorocresol | 0.1% |
| Distilled water to | 100 % |

Ball mill the steroid with a little liquid paraffin as described in Example B. that the available water to 100°C, add the chlorocresol, stir to dissolve and cool to 65°C. Melt together the beeswax, cetostearyl alcohol and cetomacrogol and maintain at 65°C. Add the steroid suspension using remaining liquid paraffin for rinsing. Add the steroid oily phase at 60°C to the chlorocresol aqueous phase at 65°C and stir rapidly while the emulsion cools over the gelling point (40°–45°C). Continue to stir at slow speed until the cream sets.

I claim:

1. 9α,12-unsubstituted $C_{19}$-steroid of the androstane or pregnane series of the formula:

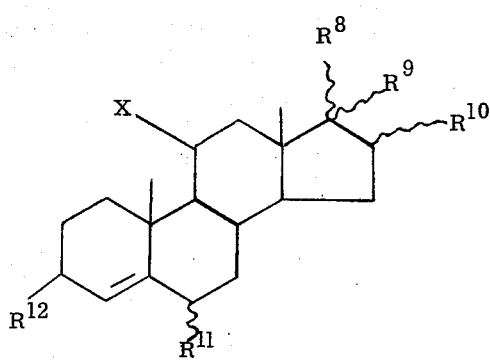

wherein X represents a chlorine or bromine atom, $R^8$ represents a member selected from the group consisting of an acetyl group; a hydroxyacetyl group; a hydroxyacetyl group esterified by a group selected from an aliphatic acyl, group having 1–9 carbon atoms in said aliphatic group, a benzoyl group, a phosphate group; and a saturated or unsaturated aliphatic hydrocarbon group which is unsubstituted or substituted by a chlorine atom;

$R^9$ represents a hydrogen atom, a hydroxy group or an aliphatic acyloxy group having 1–9 carbon atoms in the aliphatic portion, a cycloaliphatic acyloxy group having up to 7 carbon atoms in the cycloaliphatic portion, a benzoyloxy group;

or $R^8$ and $R^9$ together represent a grouping of the formula:

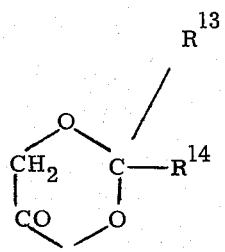

wherein $R^{13}$ represents a member selected from the group consisting of an alkyl group with 1–5 carbon atoms and an alkoxy group with 1–5 carbon atoms and $R^{14}$ represents an alkyl group with 1–5 carbon atoms or a hydrogen atom;

$R^{10}$ represents a member selected from the group consisting of a methyl group, a methylene group and a hydrogen atom;

$R^{11}$ represents a member selected from a hydrogen atom, a chlorine atom, a fluorine atom and a methyl group and;

$R^{12}$ represents an oxo group, and wherein the additional double bonds may be present at positions selected from the 1,2-position and the 6,7-position and, dienol ethers or esters thereof.

2. A steroid as claimed in claim 1 in which the acyloxy groups are acetoxy, valeryloxy, propionyloxy, hexahydrobenzoyloxy, β-phenyl propionyloxy, benzoyloxy or isobutyryloxy or butyryloxy groups.

3. A steroid as claimed in claim 1 in which the aliphatic groups are methyl, ethyl, propyl, vinyl, 2-methylprop-2-enyl, 1-methylprop-2-enyl, but-2-enyl, allyl, ethynyl or chloroethynyl groups.

4. The compound of claim 1 which is 11β-chloropregn-4-ene-3,20-dione.

5. The compound of claim 1 which is 17α-acetoxy-11β-chloropregn-4-ene-3,20-dione.

6. The compound of claim 1 which is 11β-chloro-21-hydroxy-17α-propionyloxy-16β-methylpregna-1,4-diene-3,20-dione.

7. The compound of claim 1 which is 11β-chloro-21-acetoxy-17-propionyloxy-16β-methyl-pregna-1,4-diene-3,20-dione.

8. The compound of claim 1 which is 11β-chloro-17,21-dipropionyloxy-16β-methylpregna-1,4-diene-3,20-dione.

\* \* \* \* \*